United States Patent [19]

Sogawa et al.

[11] Patent Number: 5,269,779
[45] Date of Patent: Dec. 14, 1993

[54] LASER BEAM GUIDING FIBER ASSEMBLY

[75] Inventors: Ichiro Sogawa; Shin-ichiro Niwa; Koro Yotsuya; Takafumi Uemiya; Shin-ichi Kanazawa, all of Osaka, Japan

[73] Assignee: Sumitomo Electric Industries, Ltd., Osaka, Japan

[21] Appl. No.: 892,672

[22] Filed: Jun. 4, 1992

Related U.S. Application Data

[63] Continuation of Ser. No. 460,086, Feb. 6, 1990, filed as PCT/JP89/00572, Jun. 6, 1989, published as WO89/11832, Dec. 14, 1989, abandoned.

Foreign Application Priority Data

Jun. 6, 1988 [JP] Japan ............................. 63-74911[U]

[51] Int. Cl.⁵ .............................................. A61N 5/02
[52] U.S. Cl. ................................... 606/15; 606/2; 606/7; 606/16; 606/17
[58] Field of Search .................. 128/397, 398; 606/2, 606/7, 10, 13–18

[56] References Cited

U.S. PATENT DOCUMENTS

| | | | |
|---|---|---|---|
| 4,418,688 | 12/1983 | Loeb | 606/16 |
| 4,576,177 | 3/1986 | Webster, Jr. | 606/7 |
| 4,587,972 | 5/1986 | Morantte, Jr. | 606/7 |

FOREIGN PATENT DOCUMENTS

| | | |
|---|---|---|
| 0195375 | 9/1986 | European Pat. Off. |
| 8500510 | 2/1985 | PCT Int'l Appl. |

*Primary Examiner*—David M. Shay
*Attorney, Agent, or Firm*—Cushman, Darby & Cushman

[57] ABSTRACT

A laser beam guiding fiber comprising, in a tip portion of an optical fiber, an oscillating member which oscillates the tip of the optical fiber along a direction which intersects an axis of the optical fiber can irradiate a wide range with laser beam, since the tip of the optical fiber oscillates by means of the oscillating member along the direction which intersects the axis of the optical fiber and the irradiated position with the laser beam reciprocates periodically with the oscillation.

3 Claims, 2 Drawing Sheets

LASER BEAM GUIDING FIBER ASSEMBLY

This is a continuation of application Ser. No. 07/460,086, filed on Feb. 6, 1990, filed as PCT/JP89/00572, Jun. 6, 1989, published as WO89/11832, Dec. 14, 1989, which was abandoned upon the filing hereof.

BACKGROUND OF THE INVENTION

1. Field of the Invention

The present invention relates to a laser beam guiding fiber, and in particular, relates to a laser beam guiding fiber for the use in, for example, a catheter for lasing in which laser beam irradiation cures a lesion portion.

2. Description of Related Art

Catheters for the use of lasing have been developed which removes a lesion portion such as a thrombus in a blood vessel, which a practitioner cannot directly approach, by means of irradiating with a laser beam and heat-vaporizing the portion. In such the lasing catheter, an optical fiber (a laser beam guiding fiber) is used to guide the laser beam to a tip of the catheter.

With the use of a conventional laser beam guiding fiber, since radiated light is in the form of thin beam in order to increase an irradiated energy density, there exists a following problem, for example, in the case of treating the lesion portion, such as an obstructed portion in the blood vessel in which it is difficult for the tip of the catheter to move widely.

That is, when the lesion portion would be irradiated with the laser beam widely in the case where such the lesion portion extends widely, the tip of the laser beam guiding fiber should be apart from the lesion portion, so that the irradiating energy density of the laser beam would be reduced. Therefore, it is necessary to increase an amount of the laser beam energy which enters the laser beam guiding fiber in order to irradiate the lesion portion with a sufficient amount of energy. However, when the amount of the laser beam energy is increased, the laser beam guiding fiber tends to be destroyed by the energy of the laser beam.

SUMMARY OF THE INVENTION

The present invention has been made by taking account of the above problem. It is an object of the present invention to provide a laser beam guiding fiber which can guide a large amount of laser radiating energy and irradiate all over the lesion portion with the laser beam.

A laser beam guiding fiber according to the present invention is characterized in that an oscillating member is disposed at a tip region of an optical fiber, which oscillating member oscillates the tip of the optical fiber along a direction which intersects an axis of the optical fiber.

Then, the laser beam guiding fiber according to the present invention can achieve a wide laser irradiating range since the tip of the optical fiber oscillates by means of the oscillating member along the direction which intersects the axis of the fiber and the irradiated position with the laser beam reciprocates periodically with the oscillation.

The laser beam guiding fiber according to the present invention will be hereinafter described in detail with reference to the accompanying drawings which show the embodiments of the present invention.

BRIEF DESCRIPTION OF THE DRAWINGS

Referring to the drawings.

DETAILED DESCRIPTION OF THE PREFERRED EMBODIMENTS

Figure 1:
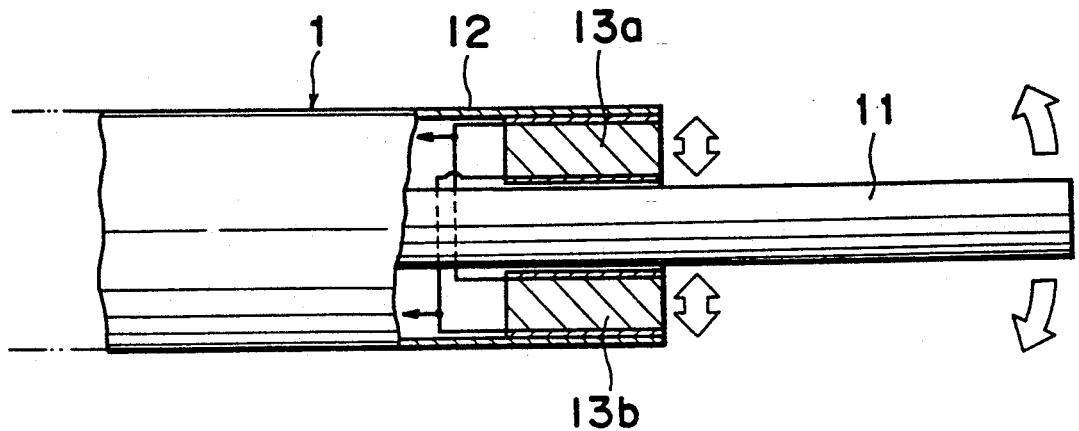
FIG. 1 shows a sectional view of one embodiment of the tip portion of the laser beam guiding fiber according to the present invention.

The laser beam guiding fiber 1 of FIG. 1 comprises an optical fiber 11, a sheath 12 in the form of an elongated cylinder which receives the optical fiber 11 and piezoelectric oscillators 13a and 13b as the oscillating members. Only the tip of the optical fiber 11 projects out of the sheath 12, and the projected portion is sandwiched between the piezoelectric oscillators 13a and 13b which are disposed inside of the tip portion of the sheath 12.

As the optical fiber 11, any type of the optical fiber can be selected from the known optical fibers such as a silica optical fiber, a silica-core plastic-cladding optical fiber, a plastic optical fiber and so on, depending on the type of the laser to be used. In particular, when excimer laser is used for the lasing, the pure silica-core optical fiber is preferably used since it can guide the excimer laser beam with a high energy density and a low loss.

Figure 2:
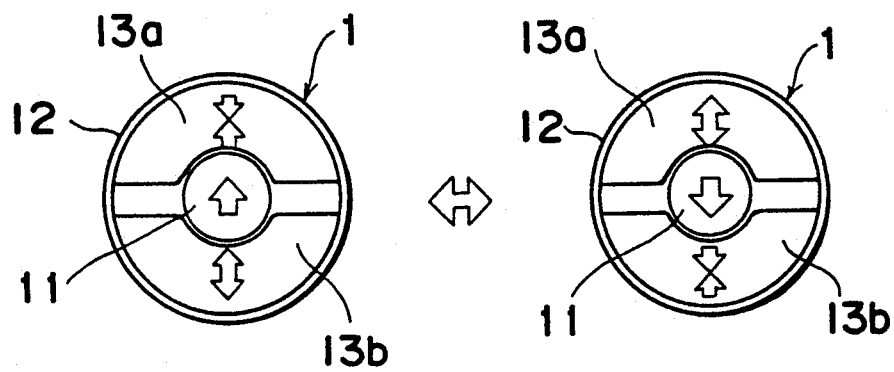
FIG. 2 shows a front view of the above embodiment showing the oscillation mode of the optical fiber.

Each of the piezoelectric oscillators 13a and 13b is formed, as shown in FIG. 2, such that it is fixed into the cylindrical space between the optical fiber 11 and the sheath 12. The oscillating direction of the piezoelectric oscillators is such that the distance between the inner circle which contacts the optical fiber 11 and the outer circle which contacts the sheath 12 is changed when the voltage is applied. In addition, the two piezoelectric oscillators 13a and 13b are, as shown with the arrows in FIG. 2, such that the phases of change in their thickness are reversed in order to smoothen the oscillation of the optical fiber sandwiched on its both sides. Thus, there are a number of ways to reverse the phases of change in the thickness of the two oscillators 13a and 13b. For example, the piezoelectric oscillators 13a and 13b which are made so as to change along the same direction one another are connected, as shown in FIG. 1, such that the phases of the applied voltage are reversed, whereby the phases of the thickness change of both oscillators are reversed.

As the piezoelectric oscillator, any known piezoelectric oscillator can be used, for example a ceramic oscillator such as a one-component system (for example $BaTiO_3$), a two-component system (for example $PbTiO_3$-$PbZrO_3$) and a three-component system (for example $Pb.(Ti,Zr).O_3$ alloyed with a third component) and a crystal oscillator such as a quartz oscillator.

The oscillating member used in the present invention is not limited to such the piezoelectric oscillator as described above, and other type of the oscillator can be used, for example, a oscillator in which an oscillating magnetic field is induced with an electromagnetic means such as a coil so that a magnetic material can be oscillated.

In the laser beam guiding fiber 1 as shown in FIG. 1, the laser beam transmitted through the optical fiber 11 is radiated from the tip of the fiber 11. Since the tip oscillates due to the piezoelectric oscillators 13a and 13b along the direction which intersects the axis of the fiber and the irradiated position with the laser beam reciprocates periodically with the oscillation of the fiber tip, the irradiated range with the laser beam can be enlarged.

Figure 3:
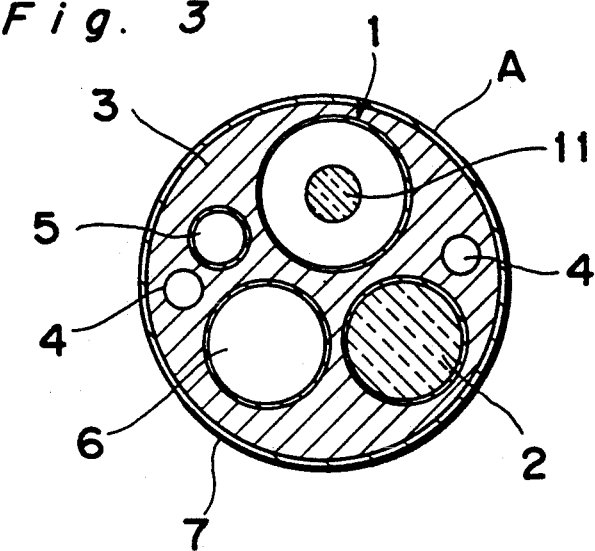
FIG. 3 shows a sectional view of one embodiment of the catheter for the use of the lasing, in which the laser beam guiding fiber is incorporated.

The laser beam guiding fiber 1 can be applied to a catheter A for the lasing, for example, as shown in FIG. 3. The lasing catheter A shown in FIG. 3 comprises, in the elongated cylindrical sheath 7, the laser beam guiding fiber 1 described above, an imaging fiber 2 for endoscope and spectral observation, a tube 5 to supply expanding gas to a balloon (not shown), for example, in order to fix the tip and a tube 6 for removing blood or dosing a medicine. In a space among the fibers 1 and 2 and the tubes 5 and 6, filled is a transparent medium 3 comprising a material transparent against visible light such as a transparent resin and a multi-component glass rich in flexibility. This transparent medium 3 can be also used as a light guide for illumination at the tip portion. Further, a bore 4 may be provided through which a controlling wire extends in order to control the tip portion of the catheter.

Figure 4:
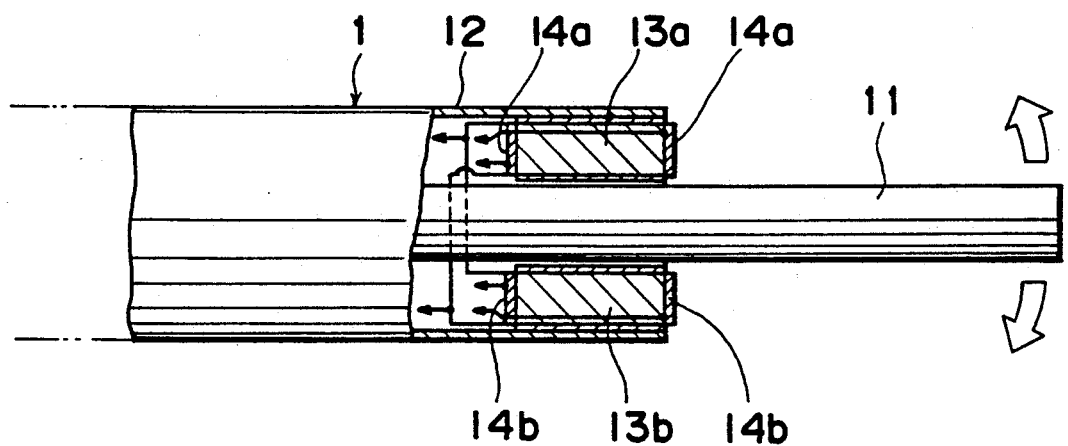
FIG. 4 shows a sectional view of a tip portion of another embodiment of the laser beam guiding fiber according to the present invention.

Another embodiment of the laser beam guiding fiber according to the present invention is shown in FIG. 4. In this embodiment, the oscillating members act as supersonic oscillators and also supersonic detectors. Oscillating electrodes 14a and 14b excite the oscillating members along the axis of the fiber and radiate supersonic wave, and also detect supersonic wave along the axis of the fiber.

Figure 5:
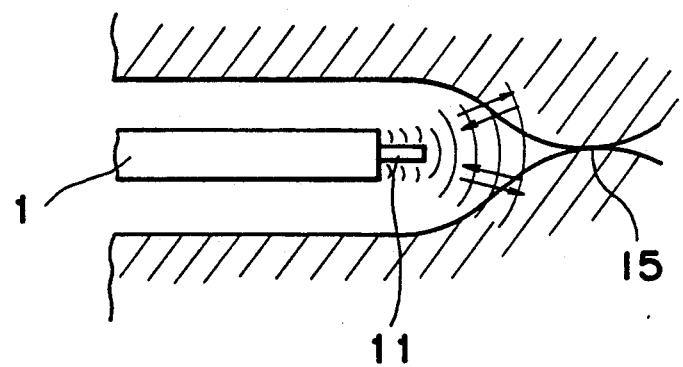
FIG. 5 shows a method in which the laser beam guiding fiber according to the present invention is used.

A method in which the laser beam guiding fiber described above is used will be described with reference to FIG. 5.

The tip of the laser beam guiding fiber is guided to the vicinity of an obstructed portion 15 in the blood vessel and the obstructed portion is irradiated with the laser beam through the fiber to be removed through vaporizing. At the same time, the oscillating members radiate supersonic wave and the reflected wave from the obstructed portion and/or the wall of the blood vessel is detected with the same oscillating members. In this way, it is possible to evaluate an extent of the vaporization with the laser beam irradiation. Also, with the reflection of supersonic wave, it is possible to measure the distance between the tip of the laser beam guiding fiber and the obstructed portion. Further, scanning of the supersonic beam in the blood vessel is possible, for example, by constituting the oscillating members with a plurality of oscillators and lagging the phases of their exciting. In such the case, the shape of the obstructed portion can be also determined. Since the supersonic wave not only reflects at the surface of tissue but also enters the inside of the tissue, it is also possible to grasp the inner configuration of the obstructed portion. In addition, by measuring Doppler shift of the wave reflected with hemocyte in blood, it is possible to determine a velocity of bloodstream, so that initiation of re-flowing of blood resulted from removal of the obstructed portion by the laser irradiation.

The laser beam guiding fiber according to the present invention is not limited to the embodiments described above and a number of modifications in design are possible within the scope of the following claims of the present invention. For example, although two piezoelectric oscillators are provided in the embodiment described above, the number of the oscillating member may be one. Further, the oscillating member is not necessarily fixed to the optical fiber. The oscillation of the fiber tip can be changed by inserting or drawing the fiber optionally in order to change the exciting position.

With the laser beam guiding fiber according to the present invention, the tip of the optical fiber oscillates along the direction which intersects the axis of the fiber and thereby the irradiated position with the laser beam reciprocates periodically with the above oscillation, so that the laser irradiating range, as a whole, can be enlarged. Therefore, since it is possible to irradiate all over the lesion portion with the laser beam while the tip of the laser beam guiding fiber can be approach sufficiently the lesion portion, safe curing over the wide range is possible at once.

What is claimed is:

1. A laser beam guiding fiber having an enlarged irradiating range comprising:
    an optical fiber having a tip portion; and
    means, in contact with said optical fiber, for oscillating said tip along a direction which intersects an axis of said optical fiber, said tip portion extending along a longitudinal direction thereof beyond said oscillating means, a said optical fiber being freely movable in said longitudinal direction to thereby change a length of said tip portion extending beyond said oscillating means.

2. The laser beam guiding fiber according to claim 1, wherein said oscillating means comprises a supersonic oscillator radiating a supersonic wave along the axis of said optical fiber and a supersonic detector for detecting a supersonic wave reflected from an object which exists along the axis of said optical fiber.

3. The laser beam guiding fiber according to claim 1, wherein said oscillating means comprises two oscillating members sandwiching said optical fiber.

* * * * *

UNITED STATES PATENT AND TRADEMARK OFFICE
CERTIFICATE OF CORRECTION

PATENT NO. : 5,269,779
DATED : December 14, 1993
INVENTOR(S) : SOGAWA ET AL

It is certified that error appears in the above-identified patent and that said Letters Patent is hereby corrected as shown below:

On title page, and column 1, line 1,

Please change:

"(54) LASER BEAM GUIDING FIBER ASSEMBLY"

to

--(54) LASER BEAM GUIDING FIBER--

Signed and Sealed this

Twenty-fourth Day of May, 1994

Attest:

BRUCE LEHMAN

Attesting Officer    Commissioner of Patents and Trademarks